US005874647A

United States Patent [19]
McGhee et al.

[11] Patent Number: 5,874,647
[45] Date of Patent: Feb. 23, 1999

[54] BENZENE HYDROXYLATION CATALYST STABILITY BY ACID TREATMENT

[75] Inventors: William D. McGhee, St. Louis, Mo.; Patrick P. B. Notté, Cantonment, Fla.

[73] Assignee: Solutia Inc., St. Louis, Mo.

[21] Appl. No.: 700,142

[22] Filed: Aug. 20, 1996

[51] Int. Cl.[6] .................................................. C07C 37/00
[52] U.S. Cl. ............................ 568/800; 502/34; 502/35; 502/71; 568/705; 568/714; 568/715; 568/716; 568/724
[58] Field of Search .................................. 568/705, 714, 568/715, 716, 729, 800; 502/34, 35, 71

[56] References Cited

U.S. PATENT DOCUMENTS

| | | | |
|---|---|---|---|
| 4,258,222 | 3/1981 | Möhring et al. | 568/863 |
| 4,579,993 | 4/1986 | Bowes et al. | 585/640 |
| 4,982,013 | 1/1991 | Gubelmann et al. | 568/771 |
| 5,001,280 | 3/1991 | Gubelmann et al. | 568/716 |
| 5,019,657 | 5/1991 | Gubelmann et al. | 568/774 |
| 5,055,623 | 10/1991 | Gubelmann et al. | 568/800 |
| 5,110,995 | 5/1992 | Kharitonov et al. | 568/800 |
| 5,171,553 | 12/1992 | Li et al. | 423/239 |
| 5,502,259 | 3/1996 | Zakoshansky et al. | 568/754 |
| 5,534,135 | 7/1996 | Dai et al. | 208/120 |

FOREIGN PATENT DOCUMENTS

| | | |
|---|---|---|
| 0 406 050 A2 | 6/1990 | European Pat. Off. . |
| 0 421 422 A2 | 4/1991 | European Pat. Off. . |
| 0 515 904 A1 | 12/1992 | European Pat. Off. . |
| 5-16179 | 2/1993 | Japan . |
| 8-198618 | 8/1996 | Japan . |
| 2 010 790 | 4/1994 | Russian Federation . |
| 2 116 974 | 3/1993 | United Kingdom . |
| WO 93/02994 | 2/1993 | WIPO . |
| WO 95/27560 | 10/1995 | WIPO . |
| WO 95/27691 | 10/1995 | WIPO . |
| WO 97/04871 | 2/1997 | WIPO . |

OTHER PUBLICATIONS

Li et al. (1992) Catalytic Decomposition of Nitrous Oxide on Metal Exchanged Zeolites; Applied Catalysis B: Environmental 1, L21–29; Elsevier Science Publishers B.V., Amsterdam.
Sobolev et al. (1993) Catalytic Properties Of ZSM–5 Zeolites in $N_2O$ Decomposition: The Role Of Iron; Journal of Catalysis 139, 435–443; Academic Press, Inc.
Sobolev et al. (1993) Stoichiometric Reaction Of Benzene With α–Form Of Oxygen On Fezsm–5 Zeolytes. Mechanism Of Aromatics Hydroxylation By $N_2O$; Journal of Molecular Catalysis 84, 117–124; Elsevier Science Publishers B.V., Amsterdam.
Panov et al. (1992) Oxidation Of Benzene To Phenol By Nitrous Oxide Over Fe–ZSM–5 Zeolites; Applied Catalysis A: General 82, 31–36, Elsevier Science Publishers B.V., Amsterdam.
Kharitonov et al. (1993) Ferrisilicate Analogs Of ZSM–5 Zeolite As Catalysts For One Step Oxidation Of Benzene To Phenol; Applied Catalysis A: General 98, 33–43, Elsevier Science Publishers B.V., Amsterdam.

Burch et al. (1993) Factors Affecting The Deactivation Of Various Zeolites Used As Catalysts For The Direct Partial Oxidation Of Benzene To Phenol; Applied Catalysis A: General 106, 167–183, Elsevier Science Publishers B.V., Amsterdam.
Burch et al. (1993) Investigation Of Zeolite Catalysts For The Direct Partial Oxidation Of Benzene To Phenol; Applied Catalysis A: General 103, 135–162, Elsevier Science Publishers B.V., Amsterdam.
Burch et al. (1993) Direct Partial Oxidation Of Benzene To Phenol On Zeolite Catalysts; Applied Catalysis A: General 86, 139–146, Elsevier Science Publishers B.V., Amsterdam.
Panov et al. (1993) Oxidation Hydroxylation using Dinitrogen Monoxide; A Possible Route For Organic Synthesis Over Zeolites, Applied Catalysis A: General, 98, 1–20, Elsevier Science Publishers B.V., Amsterdam.
Derwent abstract; JP 5 009 142.
Derwent abstract, JP 4 334 333.
Derwent abstract, JP 4 021 645.
Derwent abstract, JP 6 009 464.
Derwent abstract, JP 65 040 976.
Derwent abstract, EP 406 050.
Dvorak et al. (1970) Determination Of The Specific Copper Surface Area By Chromatographic Technique; Journal of Catalysis 18, 108–114, Academic Press, Inc.
Evans et al. (1983) On The Determination Of Copper Surface Area By Reaction With Nitrous Oxide; Applied Catalysis 7, 75–83, Elsevier Science Publishers B.V.
Iwamoto et al. (1983) Catalytic Oxidation By Oxide Radical Ions. 1. One–Step Hydroxylation Of Benzene To Phenol Over Group 5 And 6 Oxides Supported On Silica gel; The Journal of Physical Chemistry 87, No. 6, the American Chemical Society.
Ono et al. (1988) Functionalization Of Benzene By Its Reaction With Nitrogen Oxides Over Solid–Acid Catalysts, Heterogenous Catalysis and Fine Chemicals pp. 75–82, Elsevier Science Publihers B.V., Amsterdam.
Suzuki et al. (1988) Hydroxylation Of Benzene With Dinitrogen Monoxide Over H–ZSM–5 Zeolite, Chemistry Letters pp. 953–956, The Chemical Society of Japan.
Panov et al. (1990) The Role Of Iron In $N_2O$ Decomposition On ZSM–5–Zeolite And Reactivity Of The Surface Oxygen Formed, Journal of Molecular Catalysis 61, 85–97, Elsevier Sequoia.
Sobolov et al. (1991) Anomalously Low Bond Energy Of Surface Oxygen On FeZSM–5 Zeolite, Mendeleev Communications, No. 1, pp. 29–30.

(List continued on next page.)

*Primary Examiner*—Michael L. Shippen
*Attorney, Agent, or Firm*—Arnold White & Durkee

[57] ABSTRACT

A zeolite catalyst for hydroxylating benzene to phenol is treated hydrothermally with a gas comprising approximately 1–100 mole percent water at a temperature between approximately 350°–950° C., and subsequently is treated with an acid. This treatment selectively removes aluminum species from the zeolite catalyst in a manner that increases catalyst stability in phenol production without reducing the activity of the catalyst.

9 Claims, 1 Drawing Sheet

OTHER PUBLICATIONS

Zholobenko (1993) Preparation Of Phenol Over Dehydroxylated HZSM–5 Zeolites, Mendeleev Communications, pp. 23–24.

Hafele et al. (1996) Hydroxylation of Benzene on ZSM5 Type Catalysts, DGMK–Conference, Catalysis On Solid Acids And Bases pp. 243–251.

Vereshchagin et al, Conversion Of Ethane On Zeolite Catalysts In The Presence Of Oxygen And Nitrogen(I) Ox De, Izv. Akad. Nauk SSSR, (1988), 1718–1722, The enclosed is an English abstract translated from a Russina article.

Wen–Qing Xu et al., "Modification of Non–template Synthesized Ferrierite/ZSM–35 for n–Butene Skeletal Isomerization to Isobutylene," Journal of Catalysts, vol. 163, pp. 232–244 (1996).

Tsutsumi et al. "Adsorption Characteristics of Hydrophobic Zeolites," Proceedings of the International Symposium on Zeolites and Microporous Crystals, Nagoya, vol. 83, pp. 217–224 (Aug. 22–25, 1993).

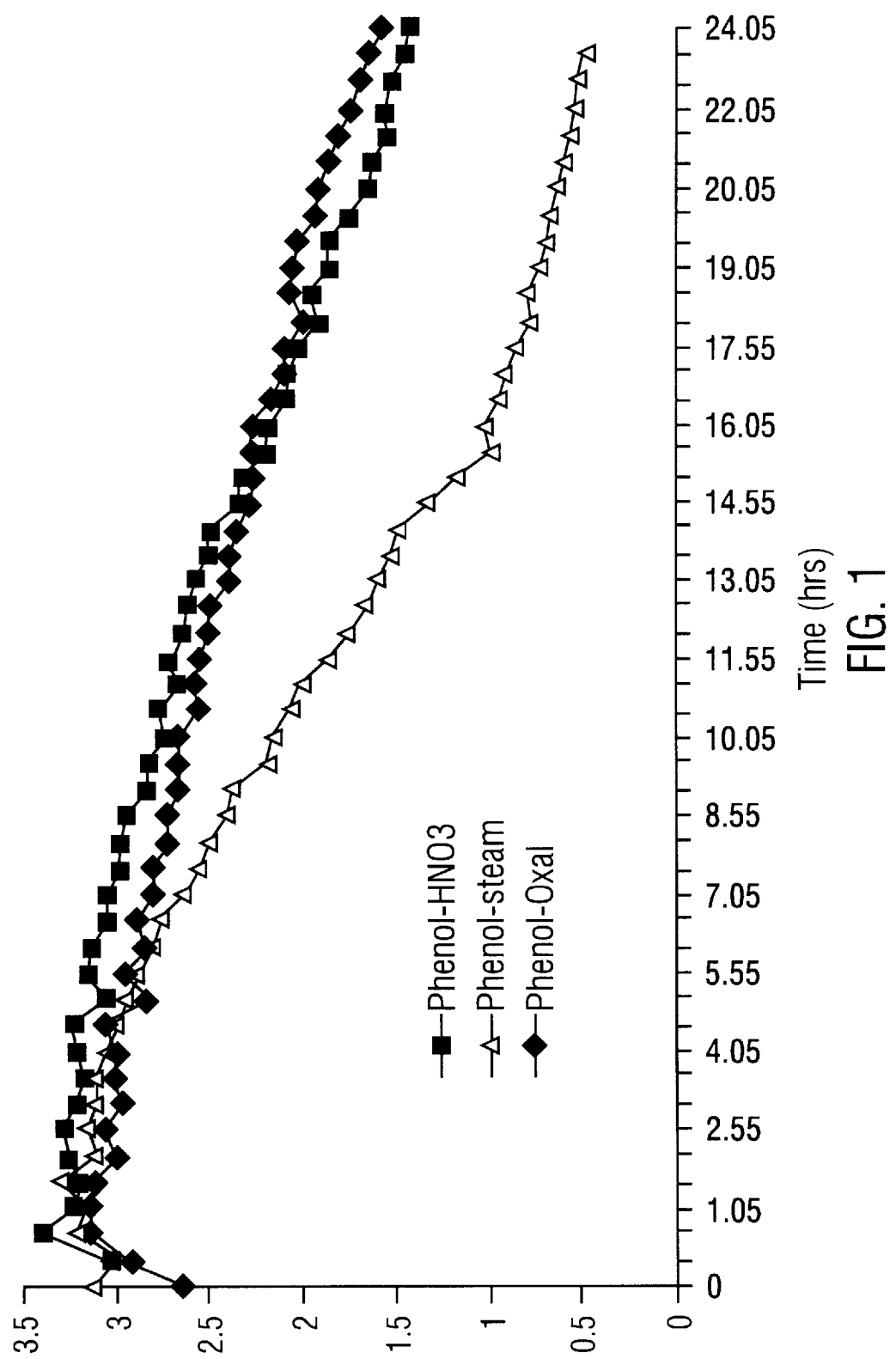

BENZENE HYDROXYLATION CATALYST STABILITY BY ACID TREATMENT

BACKGROUND OF THE INVENTION

The present invention relates to improved catalysts for use in the hydroxylation of benzene or derivatives thereof to form phenol or related compounds.

Phenol or a derivative thereof can be produced by a single-step oxidative hydroxylation of benzene or a derivative thereof, using nitrous oxide over a catalyst. For example, PCT publication WO 95/27560 describes such a process that employs a zeolite catalyst whose performance is enhanced by hydrothermal treatment. The zeolite catalyst is treated with a water vapor-containing gas phase at a temperature in the range of 350° to 950° C. Zeolite catalysts that have been hydrothermally treated in this fashion are characterized by relatively stable performance. In other words, when such a hydrothermally treated catalyst is used in a process to convert benzene to phenol by oxidation with nitrous oxide, the reduction in benzene conversion as time passes is less than it would be if the catalyst had not been hydrothermally treated.

However, a need remains for catalysts having further improved performance, so that a process for conversion of an aromatic hydrocarbon such as benzene to phenol or another desired product can be made more economical. Any improvements which increase catalyst stability and therefore increase the time between catalyst regeneration would enhance the commercial desirability of the process. Many of the efforts to date to achieve such additional catalyst improvements have focused on optimizing the hydrothermal treatment of the catalyst.

SUMMARY OF THE INVENTION

The present invention relates to a method of preparing a catalyst for oxidation of an aromatic compound such as benzene or a derivative thereof. The method comprises the steps of treating a zeolite catalyst hydrothermally with a gas comprising approximately 1–100 mole percent water at a temperature between approximately 350°–950° C., and subsequently treating the catalyst with an acid. The present invention also relates to a modified zeolite catalyst prepared by such a method, which can then be used to hydroxylate an aromatic compound.

In one embodiment, the present invention involves the following general reaction.

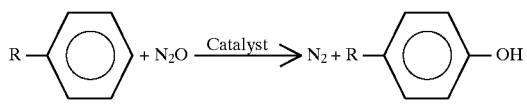

R can be a wide variety of substituents, including for example hydrogen, halogen, alkyl groups having from 1–4 carbon atoms (e.g., t-butyl, isopropyl), or a hydroxyl group. The aromatic starting material can optionally have other substituents in addition to the R group.

The present invention improves the stability of the hydroxylation catalyst without reducing the catalyst's activity by adding the additional step of acid treatment of the catalyst after the hydrothermal treatment. Improved stability in this context means an increase in catalyst half-life toward phenol production.

Without wishing to be bound by any particular theory about the mechanism of operation of the present invention, it is believed that acid treatment of the zeolite catalyst causes a selective removal of aluminum from the catalyst in a way that results in improved catalyst stability in a benzene hydroxylation process. Hydrothermal treatment of the catalyst is believed to remove some aluminum from the framework of the zeolite, which is believed to cause some improvement in selectivity and stability of the catalyst. However, the hydrothermal treatment does not remove aluminum from the bulk of the zeolite material. The acid treatment following the hydrothermal treatment removes aluminum from the cavities in the zeolite, which is believed to cause the further improvement in catalyst performance. Before the present invention it was not recognized that leaching of aluminum from a dealuminated zeolite could be accomplished in a selective manner by means of an acid treatment, nor was it recognized that this would result in further improved catalyst performance.

When a catalyst is used in a continuous process to hydroxylate benzene to phenol, the conversion gradually decreases over time. When the conversion falls too low, the catalyst must be regenerated. Regeneration can be expensive both in terms of the cost of performing the regeneration and the lost time that could otherwise be used to produce additional phenol. The catalyst of the present invention requires less frequent regeneration, making a process that uses this catalyst more economical than prior art processes. Stated another way, the catalyst preparation process of the present invention decreases the catalyst deactivation rate.

BRIEF DESCRIPTION OF THE DRAWING

FIG. 1 is a graph of the change over time in the percentage of phenol in the product stream of a benzene hydroxylation process using a zeolite catalyst in which (a) the catalyst had been hydrothermally treated ("Phenol-steam"), (b) the catalyst had been hydrothermally treated and then treated with nitric acid ("Phenol-HNO$_3$"), or (c) the catalyst had been hydrothermally treated and then treated with ammonium oxalate ("Phenol-Oxal").

DESCRIPTION OF SPECIFIC EMBODIMENTS

Aromatic compounds can be hydroxylated using the catalyst of the present invention. Preferred aromatic compounds have from about 6–18 carbon atoms. The compounds can be substituted with one or more substituents such as halogens, aliphatic hydrocarbons having from 1–4 carbon atoms, hydroxyl, carboxyl, amino, nitro, or thio groups. The improved catalysts of the present invention are especially useful in the hydroxylation of benzene and benzene derivatives such as chlorobenzene, fluorobenzene, toluene, ethylbenzene, and the like, into phenol or the corresponding substituted phenol. If phenol itself is the benzene derivative used as the reactant, the reaction products can include polyols such as hydroquinone, resorcinol, and catechol.

The catalysts used in the present invention are zeolites. Preferred types include ZSM-5, ZSM-11, and beta zeolite catalysts. These zeolites are commercially available from vendors such as Zeolyst International, UOP, Mobil, and others.

Hydrothermal treatment of the catalyst can be performed by contacting the catalyst with a gas that contains water vapor, in an amount ranging from 1–100 mole % of the gas, at an elevated temperature in the range of approximately 350°–950° C. The gas can of course include gases other than the water vapor. For example, it can include an inert gas such as nitrogen. The duration of the hydrothermal treatment of the catalyst preferably ranges from approximately 0.25 hours to approximately 8 hours. Additional details regarding hydrothermal treatment are given in PCT application WO 95/27560, which is incorporated here by reference.

The acids that are preferred for the present invention are mineral acids and small chelating acids that can enter the cavities in the zeolite. Examples of suitable acids are nitric acid, oxalic acid, hydrochloric acid, methanesulfonic acid, fluorosulfonic acid, and hydrofluoric acid. The concentration of acid used in the treatment of the catalyst preferably ranges from 0.1M–4M. The acid treatment is preferably performed at a temperature between approximately room temperature (e.g., 20° C.) and approximately 100° C., for a time ranging from approximately 0.25–8 hours.

After the catalyst has been prepared, the oxidative hydroxylation reaction is preferably performed by passing a feed gas mixture of the benzene or benzene derivative, nitrous oxide, and optionally a diluent gas such as nitrogen, argon, carbon dioxide or the like, to a bed of the zeolite catalyst at a temperature in the range of approximately 300°–600° C. The residence time in the catalyst bed is preferably between about 0.25–4 sec. The feed composition and process conditions can be varied by those skilled in the art to maximize the desired product.

The present invention can be further understood from the following examples.

Sample A was prepared by hydrothermal treatment of a commercially available zeolite catalyst referred to as 5020 (Zeolyst International) at 650° C. for one hour (50% water vapor in the gas phase), followed by addition to a silica binder, and then by calcination at 650° C. for three hours. (Si/Al=27.6)

Sample B was prepared by hydrothermal treatment of 5020 at 650° C. for one hour (50% water vapor in the gas phase), treatment with 0.5M $HNO_3$ at 70° C. for three hours, washing with water, and then addition to a silica binder, followed by calcination at 650° C. for three hours. (Si/Al=45.8)

Sample C was prepared by hydrothermal treatment of 5020 at 650° C. for one hour (50% water vapor), treatment with 0.5M ammonium oxalate at 70° C. for three hours, washing with water, and then addition to a silica binder, followed by calcination at 650° C. for three hours. (Si/Al=36.6)

The three catalysts prepared as indicated above were used to convert benzene to phenol. Performance parameters are summarized in the following table.

| Catalyst | A | B | C |
|---|---|---|---|
| Iron (ppm-XRF) | 300 | 200 | 200 |
| Bed temperature (°C.) | 482 | 481 | 479 |
| % $C_6H_6$ | 60 | 64.97 | 61 |
| % $N_2O$ | 4.11 | 4.47 | 4.12 |
| Reaction time (hr) | 24.1 | 24.1 | 24.1 |
| Avg mmol phenol/g cat. | 5.55 | 7.78 | 7.06 |
| % Phenol ($C_6H_6$) | 96 | 96.7 | 96.5 |
| % Phenol ($N_2O$) | 73.5 | 80.4 | 78.3 |
| % $N_2O$ conversion | 61.3 | 64.6 | 75.1 |
| % $N_2O$ yield | 45 | 52 | 58.8 |
| % $C_6H_6$ to diols + DPO | 2.4 | 1.8 | 2.2 |
| % $C_6H_6$ to CO + $CO_2$ | 0.5 | 0.4 | 0.4 |
| Meq coke/g catalyst | 1.47 | 1.9 | 1.49 |
| % $C_6H_6$ to coke | 1.0 | 1.0 | 0.8 |

(DPO = diphenyloxide)

FIG. 1 shows the change over time of the percentage of phenol in the product stream when the three above catalysts were used. An increase in stability for phenol production is clearly shown for catalyst samples that received acid treatment after hydrothermal treatment ("Phenol-$HNO_3$", sample C, and "Phenol-Oxal", sample B). No such improvement was seen when catalyst was acid washed prior to hydrothermal treatment. Therefore it is believed to be critical to the present invention that the acid treatment of the catalyst be preceded by hydrothermal treatment.

The preceding description of specific embodiments of the present invention is not intended to be a complete list of every possible embodiment of the invention. Persons skilled in this field will recognize that modifications can be made to the specific embodiments described here that would be within the scope of the present invention.

We claim:

1. A method for hydroxylating an aromatic compound, comprising contacting an aromatic compound with a modified zeolite catalyst, the catalyst having been prepared by a method comprising treating a zeolite catalyst hydrothermally with a gas comprising approximately 1–100 mole percent water at a temperature between approximately 350°–950° C., and subsequently treating the catalyst with an acid.

2. The method of claim 1, where the acid is a mineral acid.

3. The method of claim 1, where the acid is a small chelating acid that is capable of entering the cavities in the zeolite catalyst.

4. The method of claim 1, where the acid is selected from the group consisting of nitric acid, oxalic acid, hydrochloric acid, methanesulfonic acid, fluorosulfonic acid, and hydrofluoric acid.

5. The method of claim 1, where the zeolite catalyst is selected from the group consisting of ZSM-5, ZSM-11, and beta zeolite catalysts.

6. The method of claim 1, where the aromatic compound is benzene.

7. A method for hydroxylating an aromatic compound, comprising contacting an aromatic compound with a modified zeolite catalyst in the presence of nitrous oxide, the catalyst having been prepared by a method comprising treating a zeolite catalyst hydrothermally with a gas comprising approximately 1–100 mole percent water at a temperature between approximately 350°–950° C., and subsequently treating the catalyst with an aqueous solution of an acid selected from the group consisting of mineral acids and small chelating acids that are capable of entering the cavities in the zeolite catalyst, the concentration of the acid in the aqueous solution being about 0.1M–4M.

8. The method of claim 1, where the aromatic compound is contacted with the modified zeolite catalyst in the presence of nitrous oxide.

9. The method of claim 1, where the catalyst is treated with acid by contacting the catalyst with an aqueous solution of acid having a concentration of about 0.1M–4M.

* * * * *